United States Patent [19]

King et al.

[11] 4,261,843

[45] * Apr. 14, 1981

[54] REACTION PRODUCT OF ACIDIC MOLYBDENUM COMPOUND WITH BASIC NITROGEN COMPOUND AND LUBRICANTS CONTAINING SAME

[75] Inventors: John M. King, San Rafael; Louis deVries, Greenbrae, both of Calif.

[73] Assignee: Chevron Research Company, San Francisco, Calif.

[*] Notice: The portion of the term of this patent subsequent to Mar. 31, 1998, has been disclaimed.

[21] Appl. No.: 52,698

[22] Filed: Jun. 28, 1979

[51] Int. Cl.$^3$ .............................................. C10M 1/10
[52] U.S. Cl. .................................... 252/49.7; 252/25; 252/34.7; 252/46.4; 252/51
[58] Field of Search .................... 252/34.7, 46.4, 49.7, 252/51, 25

[56] References Cited

U.S. PATENT DOCUMENTS

| 3,140,997 | 7/1964 | Price | 252/25 X |
| 3,223,625 | 12/1965 | Cyphers et al. | 252/49.7 X |
| 3,281,355 | 10/1966 | Cyphers et al. | 252/25 X |
| 3,541,014 | 11/1970 | Le Suer | 252/25 X |

FOREIGN PATENT DOCUMENTS 790732 6/1958 United Kingdom .................... 252/49.7

*Primary Examiner*—Andrew Metz
*Attorney, Agent, or Firm*—D. A. Newell; S. R. LaPaglia; V. J. Cavalieri

[57] ABSTRACT

Antioxidant additives for lubricating oil are prepared by combining an acidic molybdenum compound and certain basic nitrogen compounds to form a molybdenum-containing compositions.

10 Claims, No Drawings

4,261,843

REACTION PRODUCT OF ACIDIC MOLYBDENUM COMPOUND WITH BASIC NITROGEN COMPOUND AND LUBRICANTS CONTAINING SAME

FIELD OF THE INVENTION

This invention relates to new lubricating oil compositions. More specifically, it relates to new lubricating oil compositions containing antioxidant molybdenum compounds.

BACKGROUND OF THE INVENTION

Molybdenum disulfide has long been known as a desirable additive for use in lubricating oil compositions. However, one of its major detriments is its lack of oil solubility. Molybdenum disulfide is ordinarily finely ground and then dispersed in the lubricating oil composition to impart friction modifying and antiwear properties. Finely ground molybdenum disulfide is not an effective oxidation inhibitor in lubricating oils.

As an alternative to finely grinding the molybdenum disulfide, a number of different approaches involving preparing salts of molybdenum compounds have been tried. One type of compound which has been prepared molybdenum dithiocarbamates. Representative compositions are described in U.S. Pat. No. 3,419,589, which teaches molybdenum (VI) dioxide dialkyldithiocarbamates; U.S. Pat. No. 3,509,051, which teaches sulfurized oxymolybdenum dithiocarbamates; and U.S. Pat. No. 4,098,705, which teaches sulfur containing molybdenum dihydrocarbyl dithiocarbamate compositions.

An alternative approach is to form dithiophosphates instead of dithiocarbamates. Representative of this type of molybdenum compound are the compositions described in U.S. Pat. No. 3,494,866, such as oxymolybdenum diisopropylphosphorodithioate.

U.S. Pat. No. 3,184,410 describes certain dithiomolybdenyl acetylacetonates for use in lubricating oils.

Braithwaite and Greene in *Wear*, 46 (1978) 405–432 describe various molybdenum-containing compositions for use in motor oils.

U.S. Pat. No. 3,349,108 teaches a molybdenum trioxide complex with diethylenetriamine for use as an additive for molten steel.

Russian Pat. No. 533,625 teaches lube oil additives prepared from ammonium molybdate and alkenylated polyamines.

Another way to incorporate molybdenum compounds in oil is to prepare a colloidal complex of molybdenum disulfide or oxysulfides dispersed using known dispersants. U.S. Pat. No. 3,223,625 describes a procedure in which an acidic aqueous solution of certain molybdenum compounds is prepared and then extracted with a hydrocarbon ether dispersed with an oil soluble dispersant and then freed of the ether. U.S. Pat. No. 3,281,355 teaches the preparation of a dispersion of molybdenum disulfide by preparing a mixture of lubricating oil, dispersant, and a molybdenum compound in water or $C_{1-4}$ aliphatic alcohol, contacting this with a sulfide ion generator and then removing the solvent. Dispersants noted to be effective in this procedure are petroleum sulfonates, phenates, alkylphenate sulfides, phosphosulfurized olefins and combinations thereof.

SUMMARY OF THE INVENTION

It has now been found that a lubricating oil additive can be prepared by combining an acidic molybdenum compound and certain basic nitrogen-containing compositions.

DETAILED DESCRIPTION OF THE INVENTION

Lubricating oil compositions containing the additive disclosed herein are effective as either fluid and grease compositions (depending upon the specific additive or additives employed) for inhibiting oxidation, imparting antiwear and extreme pressure properties, and modifying the friction properties of the oil which may, when used as a crankcase lubricant, lead to improved mileage for the vehicle being lubricated with a lubricating oil of this invention.

The precise molecular formula of the molybdenum compositions prepared in the process of this invention is not known with certainty; however, they are believed to be compounds in which molybdenum, whose valences are satisfied with atoms of oxygen or sulfur is either complexed by or the salt of one or more nitrogen atoms of the basic nitrogen containing composition used in the preparation of these additives.

The molybdenum compounds used to prepare the additives for compositions of this invention are acidic molybdenum compounds. By acidic is meant that the molybdenum compounds will react with a basic nitrogen compound as measured by ASTM test D-664 or D-2896 titration procedure. Typically these molybdenum compounds are hexavalent and are represented by the following compositions: molybdic acid, ammonium molybdate, sodium molybdate, potassium molybdate and other alkali metal molybdates and other molybdenum salts such as $MoOCl_4$, $MoO_2Br_2$, $Mo_2O_3Cl_6$, molybdenum trioxide or similar acidic molybdenum compounds. Preferred acidic molybdenum compounds are molybdic acid, ammonium molybdate, and alkali metal molybdates. Particularly preferred are molybdic acid and ammonium molybdate.

The basic nitrogen compounds are selected from those having a basic nitrogen content as measured by ASTM D-664 or D-2896. It is preferred that they be oil-soluble. These compositions are selected from succinimides, carboxylic acid amides, Mannich bases, phosphonamides, thiophosphoramides, dispersant viscosity index improvers, and mixtures thereof. These basic nitrogen containing compounds are described below (keeping in mind the reservation that each must have at least one basic nitrogen). Any of the nitrogen-containing compositions may be after-treated with e.g., boron, using procedures well-known in the art so long as the after-treated product continues to contain basic nitrogen. These after-treatments are particularly applicable to succinimides and Mannich base compositions.

The mono and polysuccinimides that can be used to prepare the lubricating oil additives described herein are disclosed in numerous references and are well known in the art. Certain fundamental types of succinimides and the related materials encompassed by the term of art "succinimide" are taught in U.S. Pat. Nos. 3,219,666, 3,172,892, and 3,272,746, the disclosures of which are hereby incorporated by reference. The term succinimide is understood in the art to include many of the amide, imide, and amidine species which are also formed by this reaction. The predominant product, however, is a succinimide and this term has been generally accepted as meaning the product of a reaction of an alkenyl substituted succinic acid or anhydride with a nitrogen containing compound. Preferred succinimides, because of their commercial availability, are those succinimides prepared from a hydrocarbyl succinic anhydride, wherein the hydrocarbyl group contains from about 24 to about 350 carbon atoms, and an ethylene amine, said ethylene amines being especially characterized by ethylene diamine, diethylene triamine, triethylene tetraamine, and tetraethylene pentamine. Particularly preferred are those succinimides prepared from polyisobutenyl succinic anhydride of 70 to 128 carbon atoms and tetraethylene pentaamine or triethylene tetraamine or mixtures thereof.

Also included within the term succinimide are the co-oligomers of a hydrocarbyl succinic acid or anhydride and a poly secondary amine containing at least one tertiary amino nitrogen in addition to two or more secondary amino groups. Ordinarily this composition has between 1,500 and 50,000 average molecular weight. A typical compound would be that prepared by reacting polyisobutenyl succinic anhydride and ethylene dipiperazine. Compositions of this type are disclosed in U.S. Ser. No. 816,063, filed July 15, 1977 the disclosure of which is hereby incorporated by reference.

Carboxylic amide compositions are also suitable starting materials for preparing the products of in this invention. Typical of such compounds are those disclosed in U.S. Pat. No. 3,405,064, the disclosure of which is hereby incorporated by reference. These compositions are ordinarily prepared by reacting a carboxylic acid or anhydride ester thereof, having at least 12 to about 350 aliphatic carbon atoms in the principal aliphatic chain and, if desired, having pendant aliphatic groups to render the molecule oil soluble which is with an amine or a hydrocarbyl polyamine, such as an ethylene amine, to give a mono or polycarboxylic acid amide. Preferred are those amides prepared from (1) a carboxylic acid of the formula $R^2COOH$, where $R^2$ is $C_{12-20}$ alkyl or a mixture of this acid with a polyisobutenyl carboxylic acid in which the polyisobutenyl group contains from 72 to 128 carbon atoms and (2) an ethylene amine, especially triethylene tetraamine or tetraethylene pentaamine or mixtures thereof.

Another class of compounds, useful for supplying basic nitrogen, are the Mannich base compositions. The Mannich base compositions are prepared from a phenol or $C_{9-200}$ alkylphenol, an aldehyde, such as formaldehyde or formaldehyde precursor such a para-formaldehyde, and an amine compound. The amine may be a mono or polyamine and typical compositions are prepared from an alkylamine such as methylamine, or an ethylene amine, such as diethylene triamine, or tetraethylene pentaamine and the like. The phenolic material may be sulfurized and preferably is dodecylphenol or a $C_{80-100}$ alkylphenol. Typical Mannich bases which can be used in this invention are disclosed in U.S. Pat. No. 4,157,309 and U.S. Pat. Nos. 3,649,229, 3,368,972 and 3,539,663, the disclosures of which are hereby incorporated by reference. The last application discloses Mannich bases prepared by reacting an alkylphenol having at least 50 carbon atoms, preferably 50 to 200 carbon atoms with formaldehyde and an alkylene polyamine $HN(ANH)_nH$ where A is a saturated divalent alkyl hydrocarbon of 2 to 6 carbon atoms and n is 1–10 and where the condensation product of said alkylene polyamine may be further reacted with urea or thiourea. The utility of these Mannich bases as starting materials for preparing lubricating oil additives can often be significantly improved by treating the Mannich base using conventional techniques to introduce boron into the composition.

The phosphoramides and phosphonamides, such as those disclosed in U.S. Pat. Nos. 3,909,430 and 3,968,157 the disclosures of which are hereby incorporated by reference, may be prepared by forming oil soluble phosphorus compound having at least one P-N bond. They can be prepared, for example, by reacting phosphorus oxychloride with a hydrocarbyl diol in the presence of a monoamine or by reacting phosphorus oxychloride with a difunctional secondary amine and a mono-functional amine. Thiophosphoramides can be prepared by reacting an unsaturated hydrocarbon compound containing from 2 to 450 or more carbon atoms, such as polyethylene, polyisobutylene, polypropylene, ethylene, 1-hexene, 1,3-hexadiene, isobutylene, 4-methyl-1-pentene, and the like, with phosphorus pentasulfide and nitrogen-containing compound as defined above, particularly an alkylamine, alkyldiamine, alkylpolyamine, or an alkyleneamine, such as ethylene diamine, diethylenetriamine, triethylenetetraamine, tetraethylenepentaamine, and the like.

Another class of nitrogen-containing compositions useful in preparing the molybdenum compositions of this invention includes the so-called dispersant viscosity index improvers (VI improvers). These VI improvers are commonly prepared by functionalizing a hydrocarbon polymer, especially a polymer derived from ethylene and/or propylene, optionally containing additional units derived from one or more co-monomers such as alicyclic or aliphatic olefins or diolefins. The functionalization may be carried out by a variety of processes which introduce a reactive site or sites which usually has at least one oxygen atom on the polymer. The polymer is then contacted with a nitrogen-containing source to introduce nitrogen-containing functional groups on the polymer backbone. Commonly used nitrogen sources include any basic nitrogen compound, especially those nitrogen-containing compounds and compositions described herein. Preferred nitrogen sources are alkylene amines, such as ethylene amines, alkyl amines, and Mannich bases.

Preferred basic nitrogen compounds for use in this invention are succinimides, carboxylic acid amides, and Mannich bases.

The process of this invention may be carried out by combining the acidic molybdenum precursor as described above in aqueous solution with a basic nitrogen-containing composition as described above. The reaction is ordinarily carried out at atmospheric pressure; however, higher or lower pressures may be used, if desired, using methods that are well-known to those skilled in the art. A diluent may be used to enable the reaction mixture to be efficiently stirred. If the mixture is sufficiently fluid to permit stirring, no diluent is necessary. A diluent which does not react with the molybdenum containing compound is desirable.

In the reaction mixture, the ratio of molybdenum compound to basic nitrogen compound is not critical; however, as the amount of molybdenum with respect to basic nitrogen, increases, the filtration of the product becomes more difficult. Since the molybdenum component probably oligomerizes, it is advantageous to add as much molybdenum as can easily be maintained in the composition. Usually the reaction mixture will have charged to it from 0.01 to 2.00 atoms of molybdenum per basic nitrogen atom. Preferably from 0.4 to 1.0, and most preferably from 0.4 to 0.7, atoms of molybdenum per atom of basic nitrogen is added to the reaction mixture.

The lubricating oil compositions of this invention can be prepared by admixing, by conventional techniques, the appropriate amount of the molybdenum-containing composition with a lubricating oil. The selection of the particular base oil depends on the contemplated application of the lubricant and the presence of other additives. Generally, the amount of the molybdenum containing additive will vary from 0.05 to 15% by weight and preferably from 0.2 to 10% by weight.

The lubricating oil which may be used in this invention includes a wide variety of hydrocarbon oils, such as naphthenic bases, paraffin bases and mixed base oils as well as synthetic oils such as esters and the like. The lubricating oils may be used individually or in combination and generally have a viscosity which ranges from 50 to 5,000 SUS and usually from 100 to 15,000 SUS at 38° C.

In many instances, it may be advantageous to form concentrates of the molybdenum containing additive within a carrier liquid. These concentrates provide a convenient method of handling and transporting the additives before their subsequent dilution and use. The concentration of the molybdenum-containing additive within the concentrate may vary from 0.25 to 90% by weight although it is preferred to maintain a concentration between 1 and 50% by weight. The final application of the lubricating oil compositions of this invention may be in marine cylinder lubricants as in crosshead diesel engines, crankcase lubricants as in automobiles and railroads, lubricants for heavy machinery such as steel mills and the like, or as greases for bearings and the like. Whether the lubricant is fluid or a solid will ordinarily depend on whether a thickening agent is present. Typical thickening agents include polyurea acetates, lithium stearate and the like.

If desired, other additives may be included in the lubricating oil compositions of this invention. These additives include antioxidants or oxidation inhibitors, dispersants, rust inhibitors, anticorrosion agents and so forth. Also anti-foam agents stabilizers, anti-stain agents, tackiness agents, anti-chatter agents, dropping point improvers, anti-squawk agents, extreme pressure agents, odor control agents and the like may be included.

Certain molybdenum products that can be prepared by the process of invention also find utility in making brake lining materials, in high-temperature structural materials, in iron and steel alloys, in cladding materials, in electroplating solutions, as components for electrical discharge machine electrodes, as fuel additives, in making self-lubricating or wear-resistant structures, as mold release agents, in compositions for phosphatizing steel, in brazing fluxes, in nutrient media for microorganisms, in making electrosensitive recording material, in catalysts for refining coal, oil, shale, tar sands, and the like or as stabilizers or curing agents for natural rubber or polymers.

What is claimed is:

1. A process for preparing a molybdenum-containing composition which comprises reacting an acidic molybdenum compound selected from the group consisting of molybdic acid, ammonium molybdate, alkali metal molybdate, bromide and chloride molybdenum salts, and molybdenum trioxide and a basic nitrogen compound selected from the group consisting of a carboxylic acid amide, Mannich Base, phosphonamide, thiophosphonamide, phosphoramide, and a dispersant viscosity index improver wherein from 0.01 to 2 atoms of molybdenum are present per basic nitrogen atom to form a molybdenum-containing complex.

2. The process of claim 1 wherein the acidic molybdenum compound is selected from molybdic acid, ammonium molybdate, and alkali metal molybdates.

3. The process of claim 2 wherein said acidic molybdenum compound is molybdic acid or ammonium molybdate, and said basic nitrogen compound is a carboxylic acid amide, or a Mannich base prepared a $C_{9-200}$ alkylphenol, formaldehyde, and an amine.

4. The process of claim 3 wherein said basic nitrogen compound is a carboxylic acid amide prepared from one or more carboxylic acids of the formula $R^2$—COOH, wherein $R^2$ is $C_{12-350}$ alkyl or $C_{12-350}$ alkenyl and a hydrocarbyl polyamine.

5. The process of claim 4 wherein $R^2$ is $C_{12-20}$ alkyl or $C_{12-20}$ alkenyl and the hydrocarbyl polyamine is tetraethylene pentaamine or triethylene tetraamine.

6. The process of claim 3 wherein said basic nitrogen compound is the Mannich base prepared from dodecyl phenol, formaldehyde, and methylamine.

7. The process of claim 3 wherein said Mannich base is prepared from a $C_{80-100}$ alkylphenol, formaldehyde, and triethylene tetraamine, tetraethylene pentaamine, or mixtures thereof.

8. The product prepared by the process of claim 1, 2, 3, 4, 5, 6 or 7.

9. A lubricating oil composition comprising an oil of lubricating viscosity and from 0.05 to 15% by weight of the product of claim 8.

10. A lubricating oil concentrate composition comprising an oil of lubricating viscosity and from 15 to 90% by weight of the product of claim 8.

* * * * *